United States Patent [19]
Sudo

[11] Patent Number: 6,007,520
[45] Date of Patent: *Dec. 28, 1999

[54] MEDICAL INSTRUMENT

[75] Inventor: Morihiro Sudo, Tokyo, Japan

[73] Assignee: Daikyo Gomu Seiko, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/941,755

[22] Filed: Sep. 30, 1997

Related U.S. Application Data

[63] Continuation of application No. 08/726,236, Oct. 4, 1996, abandoned, which is a continuation of application No. 08/017,243, Feb. 12, 1993, abandoned.

[30] Foreign Application Priority Data

Feb. 12, 1992 [JP] Japan ................................ 4-025213
Feb. 2, 1993 [JP] Japan ................................ 5-015521

[51] Int. Cl.$^6$ ............................. A61M 5/00; B32B 25/08
[52] U.S. Cl. ........................ 604/181; 264/496; 428/494; 526/281
[58] Field of Search ............................... 604/19, 29, 265, 604/266, 408; 526/113, 115, 116, 118, 119, 126, 281; 428/519, 494, 492, 339; 264/496, 494, 524, 239

[56] References Cited

U.S. PATENT DOCUMENTS

| | | | |
|---|---|---|---|
| 4,529,398 | 7/1985 | Wong et al. | 604/49 |
| 5,288,560 | 2/1994 | Sudo et al. | 428/494 |
| 5,629,398 | 5/1997 | Okamoto et al. | 526/281 |

FOREIGN PATENT DOCUMENTS

| | | |
|---|---|---|
| 0 226 956 | 7/1987 | European Pat. Off. . |
| 0226956 | 7/1987 | European Pat. Off. . |
| 0 384 694 | 8/1990 | European Pat. Off. . |
| 0384694 | 8/1990 | European Pat. Off. . |
| 0 386 896 | 9/1990 | European Pat. Off. . |
| 0386896 | 9/1990 | European Pat. Off. . |
| 0 497 567 | 8/1992 | European Pat. Off. . |
| 0 524 802 | 1/1993 | European Pat. Off. . |

OTHER PUBLICATIONS

Database WPIL, Derwent Abstract of JP-A-3 068 363.

*Primary Examiner*—Wynn Wood Coggins
*Assistant Examiner*—A. T. Nguyen
*Attorney, Agent, or Firm*—Wenderoth, Lind & Ponack, L.L.P.

[57] ABSTRACT

A medical instrument capable of maintaining medicament liquids such as pharmaceuticals, nutriments in high quality and dosing correctly and sanitarily is provided. This medical instrument comprises a material containing a resin formed of a cyclic olefin compound or a bridged polycyclic hydrocarbon compound, as a polymeric component.

18 Claims, 6 Drawing Sheets

MEDICAL INSTRUMENT

This application is a continuation of now abandoned application, Ser. No. 08/726,236 filed Oct. 4, 1996, which is a continuation of abandoned application Ser. No. 08/017,243 filed Feb. 12, 1993.

BACKGROUND OF THE INVENTION

1. Field of the Invention

This invention relates to a medical device, and more particularly, it is concerned with a medical instrument used for administering to or receiving from medical fluid, for example, syringes, transfusers (introducer), operation devices for blood gathering or blood transfusion, mechanical parts, etc.

2. Description of the Prior Art

As to the medical instruments, the varieties, performances, qualities and standards of instruments or machines are provided in the Drugs, Cosmetics and Medical Instruments Act. In this age of rapid progress of medical techniques, instruments or machines having more excellent performances than such standard values or standard items have appeared.

As a soft elastic material for a medical instrument, there is mainly used natural rubber (NR), but at the present time, isoprene rubber (IR), butyl rubber (IIR), halogenated butyl rubbers (BIIR, CIIR), nitrile rubber (NBR), styrenebutadiene rubber (BR) have widely been used in view of that these rubbers are more sanitary and have more excellent properties.

As to a synthetic resin, polyethylene (PE), polyvinyl chloride (PVC) and polypropylene (PP) have been authorized by the Japanese Pharmacopoeia of 8th Revision and applied to a number of medical instruments or machine parts.

PVC seems to be a clear and soft sanitary article, but detailed examination thereof tells a problem that a plasticizer such as dioctyl phthalate, dioctyl adipate (DOA) and tricresyl phosphate (TCP) or a stabilizer such as zinc stearate, calcium stearate and tin compounds is dissolved out in a medical fluid. The use of PVC in the future is questionable because of a problem on protection of environment such that raw material monomers of PVC remain and poisonous gases are generated when used instruments are burnt up as a waste. On the other hand, a number of studies have been made on a medical instrument for preservation of blood (Japanese Patent Publication No. 42507/1990, Japanese Patent Laid-Open Publication No. 212536/1990).

Lately, PE has widely been used, since a gas sterilization method of ethylene oxide or formaldehyde is authorized and is sanitarily excellent. In particular, ultrahigh molecular weight polyethylene is relatively excellent in softening point (130° C.) and laminated articles thereof with a vulcanized rubber, PP, nylon, PVC, etc. has being authorized. However, PE has a large disadvantage that the softening point is low.

PP has a large feature of its high softening point, but because of difficulty in obtaining a transparent article, it has been proposed to modify PP to give a transparent article which can be applied to medical instruments or pharmaceutical agents (Japanese Patent Laid-Open Publication Nos. 163144/1991 28246/1991).

Polyvinylidene chloride is generally blended with PVC to form an article because of difficulty in molding an article of polyvinylidene chloride.

Fluoro resins are excellent in sanitary property, heat resistance, acid resistance, alkali resistance, etc., but are so inferior in adhesiveness and in workability that these resins cannot be applied to parts for widely used medical instruments.

In addition, nylons, polycarbonates, polyurethanes, polyethylene terephthalates, ethylene vinyl acetate copolymers, polystyrenes, acrylic resins, thermoplastic elastomers, etc. are resins each having various properties, but having many problems from the standpoint of a raw material for a medical instrument and having no property to substitute for PE or PP.

The present invention has been made under the situation to develop an article for a medical instrument using a novel material capable of dosing a patient with a medical fluid in a very sanitary manner.

SUMMARY OF THE INVENTION

It is an object of the present invention to provide a medical instrument consisting of a material capable of sanitarily dosing a patient with a medical fluid, whereby the above described many problems can be resolved.

This object can be attained by a medical instrument consisting of a material containing a resin formed of a cyclic olefin compound or a bridged polycyclic hydrocarbon compound, as a polymeric component.

BRIEF DESCRIPTION OF THE DRAWINGS

The accompanying drawings are to illustrate the principle and merits of the present invention in detail.

FIG. 7 is a cross-sectional view of a branched pipe consisting of a cyclic resin according to one embodiment of the present invention.

DETAILED DESCRIPTION OF THE INVENTION

Figure 1:
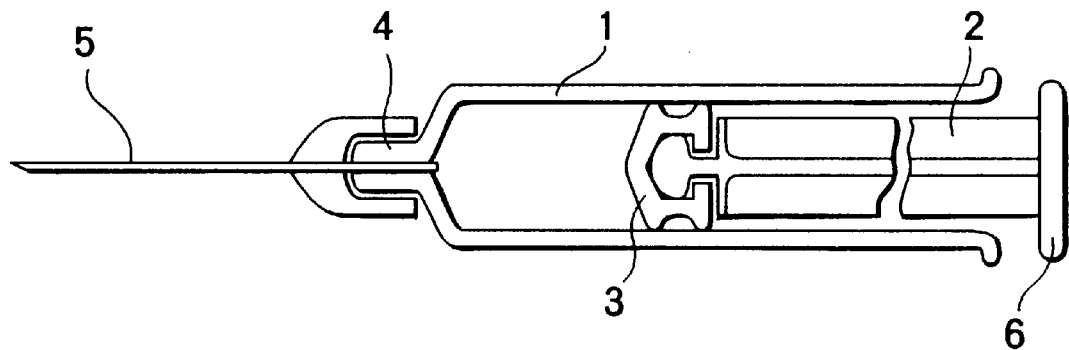
FIG. 1 is a cross-sectional view of a syringe consisting of a cyclic resin, according to one embodiment of the present invention.

The inventors have made various studies to develop a medical instrument used for dosing a patient with a medical fluid, for example, syringes, needle transfusers (introducer), operation devices for blood gathering or blood transfusion, mechanical parts, etc. while making sure of sanitary property for a long time, and consequently, have found that a resin formed of a cyclic olefin compound or a bridged polycyclic hydrocarbon compound, as a polymeric component, is effective for this purpose.

Accordingly, the present invention provides a medical instrument article consisting of a material containing a resin formed of a cyclic olefin compound or a bridged polycyclic hydrocarbon compound, as a polymeric component.

As the above described cyclic olefin compound in the present invention, there are preferably used monocyclic olefin compounds and their alkyl derivatives and acrylate derivatives.

As the above described bridged polycyclic hydrocarbon compound in the present invention, there are particularly preferably used those having at least one unsaturated bond in the ring or substituent.

In the present invention, a resin comprising the above described cyclic olefin compound or bridged polycyclic hydrocarbon compound, as a polymeric component, (which will hereinafter be referred to as "cyclic resin") can contain at least one of lower olefins, aromatic compounds or lower olefin or aromatic vinyl monomers, as a copolymeric component, and can be a mixture with olefin resins and/or synthetic rubbers.

Furthermore, the cyclic resin of the present invention is preferably one having any one of properties, a bromine number of at most 5 and a softening point of at least 90° C.

Preferred embodiments of the medical instruments according to the present invention include injection cylinders, transfer needles (introducers), parts for liquid transfusion set, instruments for gathering blood, instruments for blood transfusion, parts for blood set, artificial kidney devices of dialysis type, catheters, tubes, blood bags, syringe-cum-containers filled with two kinds of drugs, syringes consisting of the cyclic resin of the present invention, combined with the above described instruments to form one body and the like.

In the medical instrument of the present invention, a particularly preferred embodiment includes laminated articles of the cyclic resin and other resins.

Of late, characteristic resins have been developed by new techniques as to separation or purification of monomers of $C_5$ to $C_9$ fractions obtained by cracking of coal tar or naphtha and polymerization catalysts of the monomers and above all, a marked progress appears in polymers of the cyclic olefin monomers, in particular, bridged polycyclic hydrocarbon monomers.

The inventors have found that a resin comprising a cyclic olefin compound or bridged polycyclic hydrocarbon compound, as a polymeric component, is a non-crystalline material having excellent properties regarding alkali resistance, acid resistance, water proof property and chemical resistance, and having a high melting point, heat resistance, oxidation resistance and transparency, and is a very excellent resin as a medical instrument being capable of passing a test of Japanese Pharmacopoeia and being readily molded. The present invention is based on this finding.

Examples of the compound to be the polymeric component of the cyclic resin used as a medical instrument according to the present invention will further be illustrated in detail.

The cyclic olefin compounds include, for example, monocyclic olefin compounds such as:

cylopentadiene (referred to as CPD)

cyclopentene

cyclooctene

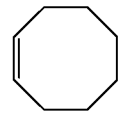

methylcyclohexene

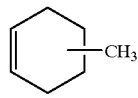

dimethylcyclohexene

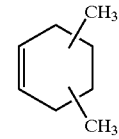

alkyl derivatives of these monocyclic olefin compounds having 1 to 3 lower alkyl groups such as methyl, ethyl group, etc. substituted, acrylate derivatives and the like.

As, the bridged Polycyclic hydrocarbon compound, it is particularly preferable to use bridged Cyclic hydrocarbon Compounds containing two or more rings, in particular, bridged polycyclic olefin compounds and derivatives thereof, or bridged polycyclic saturated hydrocarbon Compounds having unsaturated double bonds in the substituents thereof, illustrative of which are bridged polycyclic cycloalkene compounds and lower alkyl derivatives, aryl derivatives or aralkyl derivatives thereof and vinyl derivatives, allyloxycarboxy derivatives and (meth)acryloxy derivatives of bridged polycyclic cycloalkane compounds.

bicyclo[2,2,1]-2-heptoene

bicyclo[2,2,1]-2,5-heptodiene (2,5-norbornadiene)

ethyl-bicyclo[2,2,1]-2-heptoene

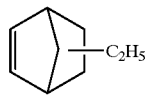

ethylidene-bicyclo[2,2,1]-2-heptoene (ethylidene-2-norbornane)

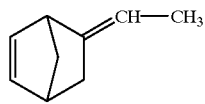

phenyl-bicyclo[2,2,1]-hepto-2-ene

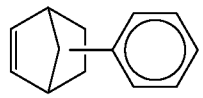

dicyclo[4,3,0]-3,8-nonadiene

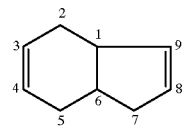

tricyclo[4,3,0,1$^{2.5}$]-3-decene

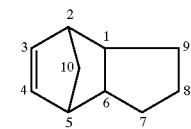

tricyclo[4,3,0,1$^{2.5}$]-3,8-decene (3,8-dihydro-dicyclopentadiene)

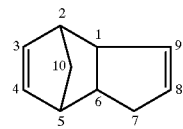

tricyclo[4,4,0,1$^{2.5}$]-3-undecene

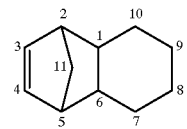

tetracyclo[4,4,0,1$^{2.5}$,1$^{7.10}$]-3-dodecene

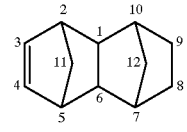

dimethyl-tetracyclo[4,4,0,1$^{2.5}$,1$^{7.10}$]-3-dodecene

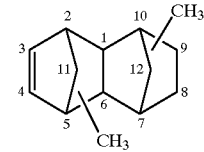

ethylidene-tetracyclo[4,4,0,1$^{2.5}$,1$^{7.10}$]-3-dodecene

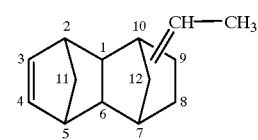

methyloxycarbonyltetracyclo[4,4,0,1$^{2.5}$,1$^{7.10}$]-3-dodecene

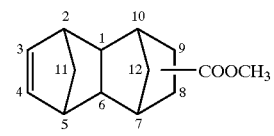

ethylidene-9-ethyltetracyclo[4,4,0,1$^{2.5}$,1$^{7.10}$]-3-dodecene

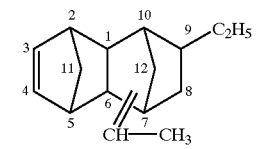

pentacyclo[4,7,0,1$^{2.5}$,0,0$^{8.13}$,1$^{9.12}$]-3-pentadecene

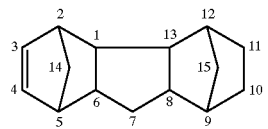

pentacyclo[6,5,1,1$^{3.8}$,0$^{2.7}$,0$^{9.13}$]-4-pentadecene

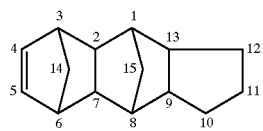

hexacyclo[6,6,1,1$^{3.6}$,1$^{10.13}$,0$^{2.7}$,0$^{9.14}$]-4-heptadecene

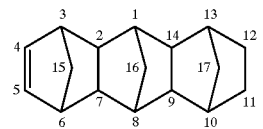

dimethyl-hexacyclo[6,6,1,1$^{3.6}$,1$^{10.13}$,0$^{2.7}$,0$^{9.14}$]-4-heptadecene

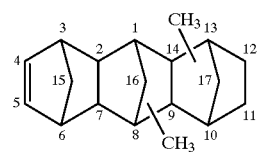

bis(allyloxycarboxy)tricyclo[4,3,0,1$^{2.8}$]-decane

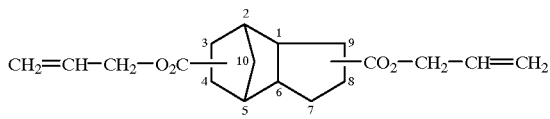

bis(metharyloxy)tricyclo[4,3,0,1$^{2.8}$]-decane

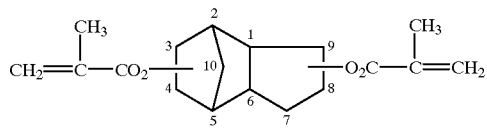

bis(acryloxy)tricyclo[4,3,0,1$^{2.5}$]-decane

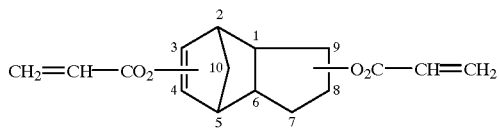

In the cyclic resin of the present invention, at least one of the above described cyclic olefin compounds and bridged polycyclic hydrocarbon compounds is used as a polymeric component and further lower olefins, aromatic compounds or vinyl monomers of lower olefins or aromatic compounds can be contained as a copolymeric component, capable of copolymerizing with these polymeric components.

Examples of these other polymeric components are ethylene, propylene, isoprene, butadiene, methylpentene, norbornene, butene, vinyltoluene and the like.

Synthesis of the cyclic resin of the present invention can be carried out in known manner, for example, as disclosed in Japanese Patent Publication Nos. 11818/1972, 43412/1983, 1442/1986 and 19761/1987, and Japanese Patent Laid-Open Publication Nos. 75700/1975, 129434/1980, 127728/1983, 168708/1985, 115916/1986, 271308/1986, 221118/1988, 243103/1088 and 180976/1990.

Specifically, the following three classified methods can be utilized:

(1) method for obtaining a bridged cyclic hydrocarbon resin, comprising subjecting a cyclopentadiene and the corresponding olefin or cyclic olefin to addition cyclization reaction (Diels Alder Reaction) to form a bridged cyclic hydrocarbon monomer, polymerizing the monomer in a solvent using an aluminum compound, vanadium compound, tungsten compound or boron compound as a catalyst to form a resinous material and purifying the resin.

(2) method for obtaining the cyclic resin of the present invention, comprising polymerizing a monomer to be the polymeric component of the cyclic resin of the present invention, for example, a lower alkylcycloalkene compound, cycloalkadiene compound, bridged polycyclic alkadiene compound, bridged polycyclic alkene compound or the like in a solvent, using a vanadium compound, aluminum compound, tungsten compound, boron compound, etc., as a catalyst to form a high molecular weight resinous material and then hydrogenating the resinous material by the use of a nickel or platinum catalyst.

(3) method for obtaining the cyclic resin of the present invention, comprising polymerizing an acryloyl derivative of a bridged polycyclic compound by light and/or an organo peroxide to obtain a bridged cyclic resin and then purifying the resin.

In the above described three polymerization reactions, a monomer of an olefin compound or aromatic compound can further be added to obtain a corresponding copolymer.

In any of the aboved described polymerization methods, the presence of the monomers used as the polymeric component, low molecular weight oligomers, metallic catalysts, etc. in the cyclic resin of the present invention is not preferable with respect to generation of odor and deterioration of the sanitary property.

Therefore, the cyclic resin of the present invention should preferably be a resin having a softening point of at least 90° C. (JIS K 2207, 2531, ring and ball method).

The cyclic resin of the present invention has preferably a bromine number of at most 5 (JIS K 2543), since if it is more than 5, coloration or discoloration takes place in a sanitary medical instrument. As a countermeasure for this coloration or discoloration, an age resistor is added.

Examples of the age resistor added to the cyclic resin of the present invention include 2-6-di-t-butyl-4-methylphneol (BHT), octadecyl-3-(4'-hydroxy-3',5'-di-t-butylphenyl) propionate (Irganox 1076—commercial name—made by Ciba Geigy Co.), tetrakis[methylene(3,5-di-butyl-4-hydroxyphenyl) propionate]-methane (Irganox 1010—commercial name—made by Ciba Geigy Co.), tocopehenol, 4,4'-thiobis(6-t-butyl-3-methylphenol) (Antage RC—commercial name—made by Kawaguchi Kagaku KK), bis(2,2,6,6-tetramethylpiperidyl) sebacate (Sanol LS-770—commercial name—made by Sankyo KK), 1,3,8-triaza-7,7,9,9-tetramethyl-n-octylspiro[4,5]decane-2,4-dione (Sanol LS-772—commercial name—made by Sankyo KK), distearyl thiodipropionate (Antigen TPS—commercial name—made by Sumitomo Kagaku KK), pentaerythritol-tetrakis(β-lauryl-thio-propionate) (Sumilizer TPD—commercial name—made by Sumitomo Kagaku KK), 1,3, 5-trimethyl-2,4,6,-tris(3,5-di-t-butyl-4-hydroxybenzyl) benzene (Ionox 330—commercial name—made by ICI) and tris(2,4-di-t-butylphenyl) phosphite (Irganox 168—commercial name—made by Ciba Geigy Co.).

These age resistors function to prevent the cyclic resin of the present invention from gelling by heat, light or oxygen. The amount of the age resistor to be added is generally 0.1 to 1 part by weight to 100 parts by weight of the cyclic resin and several age resistors can jointly be used.

The content of a cyclic olefin monomer in the cyclic resin of the present invention is preferably at least 30 weight % and the molecular weight of the cyclic resin is preferably 5000 to 100000000. A low molecular weight resin is highly viscous, but a high molecular weight resin is powdered.

In working a resin, i.e. shaping a resin article, it is preferable to use a working aid, in particular, when the shaping operation is difficult. As the working aid, there is preferably used at least one of higher fatty acids or higher fatty acid esters, silicone oils and fluorinated oils in a proportion of 0 to 10 weight % to 100 parts by weight of the cyclic resin.

The cyclic resin of the present invention has the following properties:

| | |
|---|---|
| Specific Gravity: | 0.98–1.3 (ASTM D792) |
| Tensile Strength: | 200–1000 kg/cm$^2$ (ASTM D638) |
| Tensile Elongation: | 3–300% (ASTM D638) |
| Bending Modulus: | 1–50 × 10$^4$ kg/cm$^2$ (ASTM D790) |
| Softening Point: | 90° C, or higher (ASTM D1525) |
| Transparency: | 90–100% (ASTM D1003) |
| Water Absorption Ratio: | 0.01–0.1% (ASTM D570) |
| Bromine Number: JP 12 | 0–5 (JIS K2543) |
| 48 Test method of rubber stopper for transfusion: | OK |
| 49 Test method of plastic container for transfusion: | OK |

As described above, the cyclic resin of the present invention is an ultrahigh molecular weight resin having a high softening point, excellent physical properties such as tensile strength, high toughness, high inertness to acids or alkalis, low moisture absorption, low permeability of moisture, oxygen or air, excellent cold resistance or heat resistance, non-crystalline property and transparency.

The cyclic resin or cyclic resin composition of the present invention can further contain at least one of olefin type resins, illustrative of which are various polyethylenes (PE), polypropylenes (PP), nylons including amorphous nylon, PET, PBT, ethylene-propylene copolymers, ethylene-acrylic acid copolymers, propylene-butene copolymers, polybutenes, methylbutene copolymers, ethylene-butene copolymers, methylpentene copolymers and graft- or block copolymers of olefin type compounds.

In the present invention, the above described cyclic resin or cyclic resin composition can be a mixture or alloy with a synthetic rubber. Examples of the synthetic rubber are isoprene rubbers, butadiene rubbers, ethylene-propylene rubbers, ethylene-propylene-diene-terpolymers, butadiene-isoprene copolymers, isoprene-isobutylene rubbers and the like.

When the cyclic resin of the present invention is mixed with resins or rubbers, as described above, the cyclic resin is preferably present in a proportion of at least 30 weight % to the total composition, since if the content of the cyclic resin is less than 30 weight %, the sanitary property characteristic of the present invention, e.g. alkali resistance cannot sufficiently be given so that there is little difference from medical instruments of widely used resins.

The medical instrument of the present invention can be prepared by shaping the cyclic resin or cyclic resin composition of the present invention as it is or laminating the same with another resin. Examples of the other resin are ethylene-vinylalcohol copolymer resins (EVOH), polyvinylalcohol (PVA), ethylene-vinyl acetate copolymers or saponified products thereof (EVA), nylons including amorphous nylon, ethylene-vinyl copolymer resins, PE, PP, PET, polymethylpentenes, PVDC, acrylic resins, acrylic modified resins, ethylene-propylene copolymer resins, ethylene-butene copolymer resins and graft- or block copolymers of olefin compounds.

In the above described medical instrument of the present invention, the presence of the cyclic resin and polar group-containing resin, laminated and bonded with each other, results in improvement of the quality guarantee of a content in the container. During the same time, a good bonding can be realized by the use of a laminated layer consisting of a mixture of both the resins or with an adhesives and the sanitary property of the cyclic resin can further be improved.

For the purpose of preventing a content in a medical instrument from deterioration by light (ultraviolet rays, UV) or oxidation, a UV absorber or UV shielding agent can be added to a resin to be laminated. Examples of the UV absorber or UV shielding agent are p-t-butylphenyl salicylate, 2,4-dihydroxybenzophenone, 2-hydroxy-4-methoxybenzophenone, 2(2'-hydroxy-5'-methylphenyl)-benzotriazole, 2(2'-hydroxy-3'-t-butyl-5'-methylphenyl)-5-chlorobenzotriazole, 2(2'-hydroxy-3',5'-di-t-butylphenyl)-5-chlorobenzotriazole, bis(2,2,6,6-dimethyl-4,4-piperidine) sebacate (Sanol LS 770—commercial name—made by Ciba Geigy Co.), hindered amine of polymer type (Sanol LS 944—commercial name—made by Ciba Geigy Co.), fine grain titanium oxide or zinc oxide and the like. These UV absorbers or shielding agents can be used, individually or in combination, in a proportion of 0.01 to 2 weight %.

Figure 2:
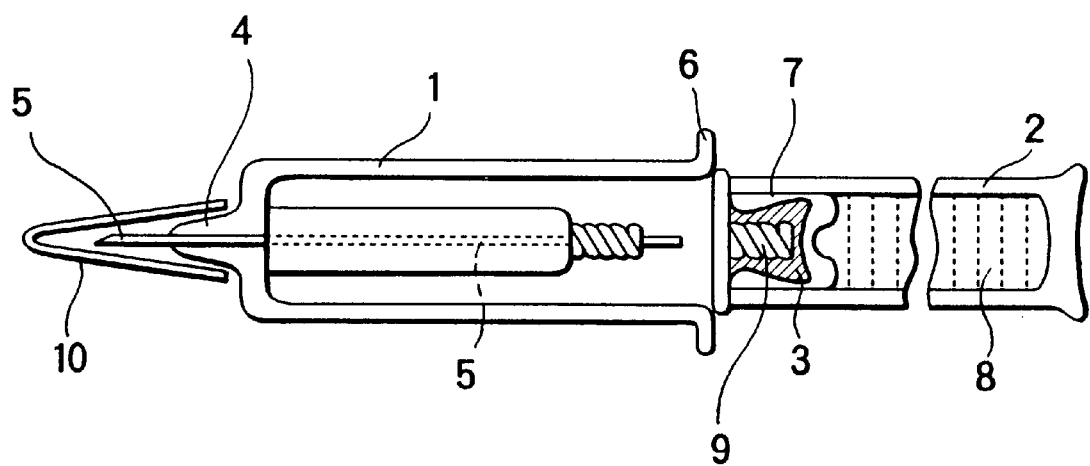
FIG. 2 is a cross-sectional view of a syringe-cum-container for a medical fluid, consisting of a cyclic resin according to one embodiment of the present invention.

A great number of kinds of the medical instruments according to the present invention can be prepared using the cyclic resin or cyclic resin composition of the present invention as described above. In particular, the cyclic resin or cyclic resin composition of the present invention can also be applied to medical instruments needing a high grade quality guaranteed. Examples of the quality standard are shown in the following:

1) Syringe (Cf. FIG. 1), Syringe-cum-Container (Cf. FIG. 2), Needless Syringe:

The quality standard is according to Offical Notification Nos. 42, 74, 413, 442 and 443 of the Ministry of Health and Welfare.

Figure 3:
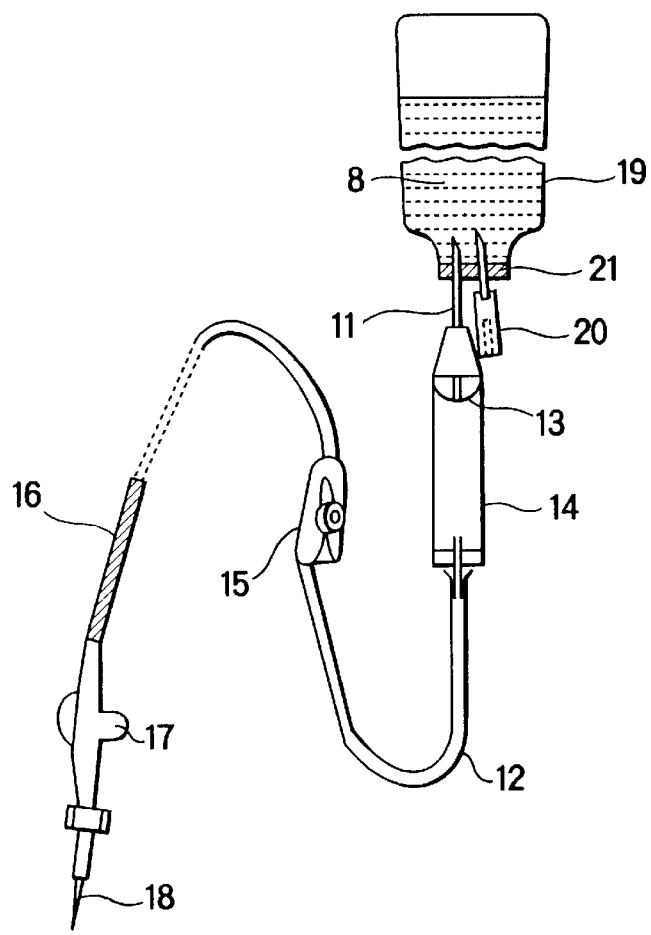
FIG. 3 is a cross-sectional view of a system for transfusion of a liquid, consisting of a cyclic resin according to one embodiment of the present invention.

2) Liquid Transfusion Set and Blood Transfusion Set (Cf. FIG. 3)

The quality standard is according to Offical Notification Nos. 42, 74 and 301 of the Ministry of Health and Welfare.

3) Instrument for Gathering Blood and Instrument for Transfusing Blood

The quality standard is according to Offical Notification Nos. 42, 74, 113, 300 and 449 of the Ministry of Health and Welfare.

4) Blood Set

The quality standard is according to Offical Notification Nos. 42, 66, 74, 134, 271 and 448 of the Ministry of Health and Welfare.

5) Artificial Kidney Device of Dialysis Type

The quality standard is according to Offical Notification Nos. 494 of the Ministry of Health and Welfare, Director of Drug Bureau.

6) Transfer Needles (Introducers), Catheters and Pipes

The quality standard is according to self-imposed control. Catheters have a standard by Nippon Iryo Kizai Kyokai (Japanese Medical Device or Material Association).

A sanitary and high grade medical instrument capable of satisfying the required quality standard can be obtained by forming these medical instruments or mechanical parts of the cyclic resin or cyclic resin composition of the present invention, or laminating the same with the cyclic resin or cyclic resin composition of the present invention.

A method of molding or laminating a medical instrument according to the present invention can be carried out by the known olefin resin molding technique. For example, such a technique consists in heating the cyclic resin or cyclic resin composition of the present invention by a screw, extruding into a metallic mold for a product, cooling and then taking the product out of the metallic mold. Furthermore, the cyclic resin of the present invention is heated and blown by an injection blow system, thus forming in a container, tube or mold for a medical instrument.

EXAMPLE

Synthesis methods of the cyclic resin according to the present invention and production processes of medical instruments using the resin or resin composition according to the present invention will be illustrated in detail without limiting the same.

Synthetic Example 1 of Cyclic Resin: DCP Polymer 3.6 liters of purified and dehydrated toluene and 1.2 kg of tricyclo[4,3,0,1$^{2.5}$]-3,8-decene (DCP) were charged in a reactor of 10 liters, equipped with a stirrer, to which 72 g of triethylaluminum, 236 g of triethylamine and 62 g of titanium tetrachloride were added in a nitrogen atmosphere at 5° C., and the mixture was heated to 25° C. and stirred for 24 hours to effect polymerization. Then, the reaction was stopped by adding methanol and the resulting resin was precipitated with methanol, followed by washing with acetoneisopropyl alcohol (1:1) and drying in vacuum at a low temperature, thus obtaining 800 g of a polymer.

The thus obtained polymer was charged in an autoclave of 5 liters, equipped with a stirrer, in the form of a 10 weight % solution in cyclohexane, to which 25 g of palladium carbon was added in a hydrogen atmosphere, followed by replacing by hydrogen, raising the temperature to 120° C. and supplementing hydrogen at a hydrogen pressure of 70 atm to effect hydrogenation for 12 hours. After the hydrogenation, the reaction mixture was subjected to centrifugal separation of the catalyst and then to precipitation in a large amount of a mixed solvent of acetone-isopropyl alcohol (1:1). To 100 parts by weight of the resulting resin were added 0.4 part by weight of BHT and 0.1 part by weight of Antigen TPS (commercial name), as an age resistor, thus obtaining 560 g of a resin (referred to as Resin (a)) having a softening point of 152° C. and a bromine number of 0.2.

Synthetic Example 2 of Cyclic Resin: DCP-Ethylene Copolymer

In a reaction vessel of 10 liters, equipped with a stirrer and dropping funnel, were charged 5 liters of purified and dehydrated toluene and then 350 g of purified and dehydrated DCP, to which maintaining the temperature at lower than 3° C., 105 g of ethylaluminum sesquichloride and 110 g of dichloroethoxyoxovanadium, as a catalyst, were dropwise added while passing a mixed gas of dry ethylene and nitrogen gas (1:2) and stirring at a temperature of 20° C. for 2 hours, thus effecting the polymerization. The copolymerization was then stopped by the use of 30 ml of methanol. A copolymer was precipitated in methanol, washed with acetone and subjected to drying in vacuum at a low temperature, thus obtaining 312 g of a copolymer.

The thus obtained copolymer was charged in a 5-liter autoclave, equipped with a stirrer, in the form of a 10 weight % solution in cyclohexane, to which 25 g of palladium carbon was added in a hydrogen atmosphere, followed by replacing by hydrogen and raising the temperature to 120° C. with agitation. Then, the hydrogen pressure was raised to 70 atm at the same temperature and hydrogen was supplemented at the same pressure to effect hydrogenation for 10 hours. After the hydrogenation, the reaction mixture was subjected to centrifugal separation of the catalyst and then to precipitation in a large amount of a mixed solvent of acetone-isopropyl alcohol (1:1), followed by filtering. To 100 parts by weight of the resulting copolymer were added 0.6 part by weight of BHT, followed by drying in vacuum, thus obtaining 300 g of a resin (referred to as Resin (b)) having a softening point of 146° C. and a bromine number of 0.1.

Synthetic Example 3 of Cyclic Resin: Copolymer of Bridged Polycyclic Hydrocarbon and Monocyclic Olefin In a reaction vessel of 10 liters, equipped with a stirrer, were charged 4.5 liters of purified and dehydrated toluene and 300 g of mixed monomers of purified and dehydrated hexacyclo[6,6,1,1$^{3.8}$,1$^{10,13}$,0$^{2.7}$,0$^{9.14}$]-4-heptadecene and cyclopentene (1:1), to which 90 g of ethylaluminum sesquichloride and 15 g of dichloroethoxyoxovanadium were dropwise added in a nitrogen atmosphere at a temperature of at most 5° C. After raising the temperature to 10° C., the reaction mixture was stirred for 24 hours to effect the polymerization. The polymerization was then stopped by the use of 150 ml of methanol and the copolymer was precipitated in methanol, followed by washing and filtering. The copolymer resin was then hydrogenated in an analogous manner to Synthetic Example 2. 0.3 part by weight of Irganox 1076 (commercial name) was added to 100 parts by weight of the resulting copolymer, uniformly mixed and dried in vacuum to obtain 160 g of a resin (referred to as Resin (c)) having a softening point of 136–156° C. and a bromine number of 0.2.

Synthetic Example 4 of Cyclic Resin

In a reaction vessel of 10 liters, equipped with a stirrer, were charged 5 liters of purified and dehydrated cyclohexane and 300 g of purified and dehydrated dimethyltetracyclo[4,4,0,1$^{2.5}$,1$^{7.10}$]-3-dodecene, to which 20 g of dichloroethoxyoxovanadium and 110 g of ethylaluminum sesquichloride were dropwise added in a nitrogen atmosphere at a temperature of at most 5° C. A mixed gases of nitrogen gas:hydrogen gas (150:1) was passed therethrough at a temperature of 10° C. for 15 hours to effect polymerization. The polymerization was then stopped by the use of 1000 ml of isopropyl alcohol and the polymer was precipitated in isopropyl alcohol, followed by washing. 0.1 part by weight of Irganox 168 (commercial name) and 0.2 part by weight of Ionox 330 (commercial name) were added to 100 parts by weight of the resulting polymer and dried in vacuum to obtain 182 g of a resin (referred to as Resin (d)) having a softening point of 141–150° C.

Synthetic Example 5 of Cyclic Resin 500 g of bis(methacryloxy)tricyclo[4,3,0,1$^{2.5}$]-decane and 500 g of cyclohexane were charged in a reactor of 5 liters, equipped with a stirrer, to which 30 g of benzoyl peroxide was added with passing nitrogen gas, followed by uniformly mixing and gradually heating to 120° C. and effecting the polymerization reaction for 7 hours. After removing the solvent, 30 g of t-butylperoxybenzoate and 3 g of 4,4'-thiobis(6-t-butyl-3-methylphenol) were uniformly added, heated at a mold temperature of 170° C. for 10 minutes to obtain a resinous powder and adequately washed with warm water, thus obtaining a resin (referred to as Resin (e)) having a softening point of at least 120° C. and a bromine number of 4.3.

Synthetic Example 6 of Cyclic Resin: Bridged Polycyclic Compound

To a reactor of 2 lters, equipped with a stirrer, were charged 250 g of methyloxycarbonyltetracyclo[4,4,0,1$^{2.5}$, 1$^{7.10}$]-3-dodecene, 1000 ml of 2-dichloroethane, 1.9 g of 1-hexene, 46 ml of a chlorobenzene solution of 0.05 mol/liter of tungsten hexachloride as a catalyst, 35 ml of a 1,2-dichloroethane solution of 0.1 mol/liter of paraldehyde and 19 ml of a toluene solution of 0.5 mol/liter of triisobutylaluminum in a nitrogen atmosphere, and the polymerization was carried out at 60° C. for 10 hours. 50 ml of methanol was added to the polymerization system to stop the polymerization, the solvent was evaporated and the product was washed with a mixed solution of acetonemethanol (1:1) and dried in vacuum. The polymerized product was dissolved in 4500 ml of tetrahydrofuran, to which 23 g of a palladium-alumina catalyst containing 5 weight % of palladium was added, and the mixture was then subjected to hydrogenation reaction at a temperature of 170° C. and a hydogen gas pressure of 100 kg/cm$^2$ for 5 hours. Then, the product was treated in an analogous manner to the treatment after the hydrogenation in Synthetic Example 1 of Cyclic Resin to obtain a polymerized resin. 0.5 part by weight of BHT was added to 100 parts by weight of the resin to obtain a resin (referred to as Resin (f)) having a softening point of at least 132° C. and a bromine number of 0.05.

Synthetic Example 7 of Cyclic Resin

In a reaction vessel of 10 liters, equipped with a stirrer, were charged 5 liters of purified and dehydrated toluene, to which 152 g of purified and dehydrated tetracyclo[4,4,0, 1$^{2.5}$1,$^{7.10}$]-3-dodecene, 19 g of methylcyclohexene, and 18 g of ethylaluminum sesquichloride and 11 g of vanadium oxytrichloride were added and mixed in a nitrogen atmosphere at a temperature of at most 5° C. Mixed gases of dried ethylene gas:nitrogen gas (1:2) was passed therethrough from a gas feed pipe, the temperature was raised to 10° C. and the polymerization reaction was carried out using 15 liters of the mixed gas for 1 hour. The polymerization was then stopped by the use of 50 ml of methanol and the polymer was precipitated in a large amount of methanol, followed by washing with a mixed solvent of acetone-isopropyl alcohol (1:1). 0.3 part by weight of Irganox 1070 (commercial name) was added to 100 parts by weight of the resulting polymer to obtain a resin (referred to as Resin (g)) having a softening point of at least 124° C. and a bromine number of 0.5.

Synthetic Example 8 of Cyclic Resin

In a reaction vessel of 10 liters, equipped with a stirrer, were charged 7 liters of purified and dehydrated toluene, to which 930 g of tetracyclo[4,4,0,1$^{2,5}$,1$^{7.10}$]-3-dodecene, 70 g of bicyclo[2,2,1]-2-heptoene, 5 g of 1-hexane, 6 g of tungsten hexachloride and 7 g of tetraphenyltin were added, followed by effecting the polymerization at a temperature of 50° C. for 3 hours. After the polymerization, methanol was added thereto to precipitate a resin and the resin was washed with a mixed solution of acetone-methanol (1:1) and dried in vacuum to obtain 980 g of a resin. The resulting resin was hydrogenated in an analogous manner to Synthetic Example 1, thus obtaining 930 g of a resin having a softening point of 155–160° C. During use of the resin, 0.5 weight % of BHT was added to 930 g of the resin (which will be referred to as Resin (h)).

Synthetic Example 9 of Cyclic Resin

In a reaction vessel, equipped with a stirrer, were mixed 600 g of tetracyclo[4,4,0,1$^{2.5}$,1$^{7.10}$]-3-dodecene, 140 g of dicyclopentadiene, 180 g of pentacyclopentadecadiene, 760 g of 1-hexene and 2700 g of toluene, purified and dried, to which 18 g of triethylaluminum, 36 g of triethylamine and 5.5 g of titanium tetrachloride were added in the form of a solution in purified and dried toluene, while stirring, in a nitrogen atmosphere at a temperature of 25° C. The polymerization was carried out at the same temperature for 5 hours. Acetone-isopropyl alcohol (1:1) was added to the reaction vessel to stop the polmerization and a resin was precipitated, filtered and dried in vacuum. Then, the resin was dissolved in 6000 ml of cyclohexane and subjected to hydrogenation by adding 60 g of palladium-carbon in a hydrogen gas atmosphere at a hydrogen pressure of 60 kg/cm$^2$ and a temperature of 155° C. for 5 hours. The resin was filtered, precipitated in acetone-isopropyl alcohol (1:1) and washed, followed by adding 0.2 weight % of BHT thereto and drying in vacuum to obtain 360 g cf a resin (referred to as Resin (i)) having a softening point of 186° C.

Examples 1 to 7 and Comparative Example 1

Using Resins (a) to (g), obtained in Synthetic Examples of Cyclic Resins as described above, syringes with shapes of FIG. 2 were molded according to compositions and molding conditions as shown in Table 1 (Examples 1 to 7).

For comparison, a syringe was similarly molded according to conditions shown in Table 1 using PP (Polypro 6200 E—commercial name—made by Mitsubishi KK). (Comparative Example 1).

In FIG. 2, 1: barrel; 2: plunger; 3: gasket; 4: cylinder nozzle 5: injection needle; 6: flange; 7: cyclic resin coating of the invention; 8: medicament liquid; 9: threaded engagement part; 10: injection needle cap

TABLE 1

|  | Examples | | | | | | | Comparative Example |
|---|---|---|---|---|---|---|---|---|
| Items | 1 | 2 | 3 | 4 | 5 | 6 | 7 | 1 |
| Composition (weight parts) | | | | | | | | |
| Resin | (a) 100 | (b) 100 | (c) 100 | (i) 100 | (e) 100 | (f) 100 | (g) 100 | PP 100 |
| Compounding Agent | Silicone Oil 2 | Silicone Oil 2 Fatty Acid Ester 1 | Silicone Oil 0.5 Fatty Acid Ester 1 | Fatty Acid Ester 2 | Fluorine Type Mold Lubricant Used in Metallic Mold | Fatty Acid Ester 2 | Fatty Acid Ester 2 | Fatty Acid Ester 2 |
| Molding Conditions | | | | | | | | |
| Temperature in Extrusion Screw (±3° C.) | 180 | 200 | 170 | 180 | 180 | 170 | 170 | 180 |
| Metallic Mold Temperature for Injection Cylinder (° C.) | 70 | 90 | 60 | 60 | — | 60 | 70 | 80 |

The syringe-cum-container holding a medicament liquid or distilled water for injection in its injection barrel was further subjected to a sanitary test according to "49 Test Method of Plastic Container for Liquid Transfusion" of JP 12, thus obtaining results as shown in Table 2:

TABLE 2

|  | Examples | | | | | | | Comparative Example | JP 12 |
|---|---|---|---|---|---|---|---|---|---|
|  | 1 | 2 | 3 | 4 | 5 | 6 | 7 | 1 | Standard |
| Transparency and Appearance | clear | clear | clear | clear | clear | clear | clear | opaque | |
| Steam Permeability | 0.12 | 0.16 | 0.10 | 0.15 | 0.18 | 0.10 | 0.13 | 0.10 | <0.20% |
| Heavy Metal (ppm) | <0.05 | <0.05 | <0.05 | <0.05 | <0.05 | <0.05 | <0.05 | <0.5 | |
| Lead (ppm) | <0.03 | <0.03 | <0.03 | <0.03 | <0.03 | <0.03 | <0.03 | <0.3 | |
| Cadmium (ppm) | <0.03 | <0.03 | <0.03 | <0.03 | <0.03 | <0.03 | <0.03 | <0.3 | |
| Fired Residue (%) | <0.1 | <0.1 | <0.1 | <0.1 | <0.1 | <0.1 | <0.1 | <0.1 | <0.10 |
| Eluate Test | | | | | | | | | |
| Property | * | * | * | * | * | * | * | * | colorless, clear |
| Foaming (min) | 0.5 | 0.5 | 0.5 | 0.5 | 0.5 | 0.5 | 0.5 | 0.5 | <3 minutes |
| pH | 0.4 | 0.3 | 0.4 | 0.5 | 0.7 | 0.3 | 0.4 | 0.4 | <1.5 |
| Cl salt (ppm) | 0.5 | 0.4 | 0.3 | 0.4 | 0.6 | 0.4 | 0.3 | 0.3 | |
| $SO_4$ Salt (ppm) | <0.5 | <0.5 | <0.5 | <0.5 | <0.5 | <0.5 | <0.5 | <0.5 | |
| $PO_3$ Salt (ppm) | <0.3 | <0.3 | <0.3 | <0.3 | <0.3 | <0.3 | <0.3 | <0.3 | |
| $NH_4$ Salt (ppm) | <0.5 | <0.5 | <0.5 | <0.5 | <0.5 | 0.3 | <0.5 | <0.5 | |
| $KMnO_4$ Reducing Material (ml) | 0.6 | 0.4 | 0.6 | 0.8 | 1.0 | 0.3 | 0.6 | 0.6 | <1.0 ml |
| Evaporation Residue (mg) | 0.3 | 0.2 | 0.4 | 0.5 | 0.8 | 0.4 | 0.5 | 0.5 | <1.0 mg |
| UV Absorption Spectrum | 0.02 | 0.02 | 0.02 | 0.03 | 0.05 | 0.02 | 0.03 | 0.05 | <0.05 |
| Acute Toxicity Test | normal | normal | normal | normal | normal | normal | normal | normal | normal |
| Subcutaneous Reaction Test | normal | normal | normal | normal | normal | normal | normal | normal | normal |
| Feverish Material Test | OK | OK | OK | OK | OK | OK | OK | OK | OK |
| Hemolytic Material Test | no | no | no | no | no | no | no | no | no |
| Transplantation Property Test | normal | normal | normal | normal | normal | normal | normal | normal | normal |

Note)
*colorless and clear

As shown in Table 2, the articles of the present invention satisfy the standards and exhibit normal property, but the article of Comparative Example 1 is opaque and is not suitable as a container for injection. When using commercially available resins, PVC or PE, a molded article deforms or adheres by a high pressure steam sterilization treatment at a temperature of 120° C. for 60 minutes corresponding to the test conditions of JP 12. This means that such a comparative article is a disqualified article. The molded articles of the cyclic resins of the present invention are transparent and do not deform even by the high pressure steam sterilization treatment.

The details of the tests shown in Table 2 are illustrated below:

JP 12 Test

Property of Elution Test, Foaming, pH, Zn, $KMnO_4$ Reducing Property,

Evaporation Residue, UV (ultraviolet ray) Absorption Spectrum

A sample is mixed with water in an amount of 10 times as much as the sample and then heated and extracted with high pressure steam at 120° C. for 1 hour. In view of that DIN or BS is carried out by heating at 121° C. for 30 minutes, it is apparent that the extraction condition of JP 12 is the severest.

Acute Toxicity, Subcutaneous Reactions, Feverish Materials, Hemolytic Materials and Transplantation Tests:

These tests are carried out according to JP 12, which are somewhat different from those of DIN, BS or USP.

Examples 8 to 13

Production and Sanitary Test of Liquid Transfusion Set and Blood Transfusion Set A liquid transfusion set means a series of instrument for dosing a vein with pharmaceuticals such as antibiotics, anticancer medicines, etc., nutrients such as grape sugar, amino acids, vitamines, electrolytes, etc., water, high calorie injecting mixed liquid medicines, a discharge regulator 15 (flow rate control clamp), coupling tubes 12 and 16, a dripping tube 14 (dripping cylinder) and an introducing needle 11 (liquid medicine injecting needle, bottle needle, container needle, liquid transfusion needle). The liquid transfusion needle 18 includes a vein needle and decurrent needle, mainly consisting of cold rolled stainless steel material. The introducing needle 11 is formed of a resin or stainless steel. A blood transfusion set mans a series of instruments ordinarily comprising a blood transfusion needle 18, an introducing needle 11, a coupling tube 12, a dripping tube 14 and a filtering device 13 (filtering net), which is similar to the liquid transfusion set and thus handled equally thereto as a standard of medical instrument.

Using the cyclic resin of the present invention, the liquid transfusion set as shown in FIG. 3 was molded. Each of the parts of the set was molded in known manner by a metallic mold, i.e. by heating and melting a raw material resin in a screw, extruding and forming in a metallic mold and cooling to thus obtain a molded part. The raw material resins, compositions and molding conditions are as shown in Table 3. In Table 3, 1) is liquid isoprene rubber and 2) is Japanese Patent Laid-Open Publication No. 68363/1991.

In FIG. 3, 8: medicament liquid; 11: introducing needle; 12: coupling tube; 13: filtering net; 14: dripping tube; 15: discharge regulator; 16: rubber tube; 17: octopus tube; 18: liquid transfusion needle 19: container; 20 air feed needle; 21: rubber stopper;

TABLE 3

Figure 4:
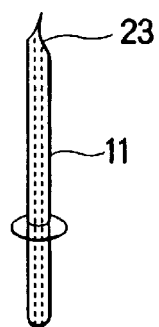
FIG. 4 is a cross-sectional view of an injection needle consisting of a cyclic resin according to one embodiment of the present invention.
Figure 5:
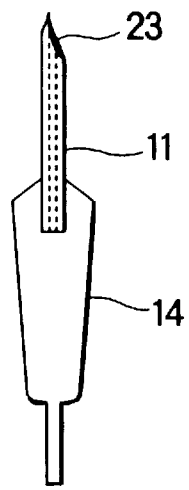
FIG. 5 is a cross-sectional view of an injection needle with a dripping cylinder, consisting of a cyclic resin according to one embodiment of the present invention.
Figure 6:
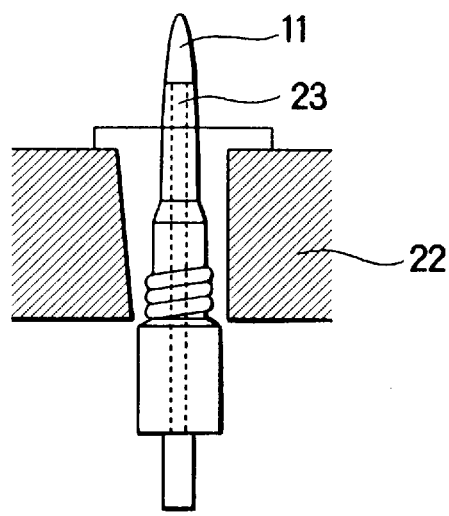
FIG. 6 is a cross-sectional view of a state of an injection needle inserted in a stopper for a container, consisting of a cyclic resin according to one embodiment of the present invention.

| | Examples | | | | | |
|---|---|---|---|---|---|---|
| Items | 8 | 9 | 10 | 11 | 12 | 13 |
| Part of Instrument | Octopus Tube | Rubber Tube | Discharge Regulator | Coupling Tube | Dripping Tube | Introducing Needle |
| Mark in FIG. | 17 | 16 | 15 | 12 | 14 | 11 |
| Composition (weight parts) | | | | | | |
| Resin | (d) 100 | (d) 100 | (b) 100 | (d) 100 | (a) 100 | (b) 100 |
| Compounding Agent | Natural Rubber 5 IR[(1)] 10 | Natural Rubber 10 IR[(1)] 10 Dynamic Crosslinked Rubber of EPDM[(2)] 10 | Fatty Acid Ester 2 | IR[(1)] 10 Dynamic Crosslinked Rubber of EPDM[(2)] 10 | Fatty Acid Ester 1 | Silicone Oil 1 |
| Molding Conditions | | | | | | |
| Extrusion Screw Temperature (° C.) | 180 ± 3 | 18 ± 3 | 200 ± 5 | 180 ± 3 | 170 ± 3 | 200 ± 5 |
| Metallic Mold Temperature (° C.) | 60 ± 2 | 60 ± 2 | 80 ± 2 | 60 ± 2 | 60 ± 2 | 80 ± 2 | transfusion liquids and the like by dripping from a container such glass bottle, plastic bottle or plastic bag. FIG. 3 shows a typical example of a liquid transfusion set and FIG. 4 to 6 show examples of parts of the set, comprising a liquid transfusion needle 18 for injecting in the veins of a human body, an octopus tube 17 of Y-type or -type, used for These parts were assembled and fusion-bonded to obtain a liquid transfusion set. The tests of properties or performances and saniatry tests of the thus resulting liquid transfusion set were carried out according to the Official Notification Nos. 301 and 42 of the Ministry of Health and Welfare, thus obtaining results shown in Table 4.

TABLE 4

|  | Examples | | | Standards of Notification of Ministry of |
|---|---|---|---|---|
|  | 11 | 12 | 13 | Health and Welfare |
| Part of Instrument | Coupling Tube | Dripping Tube | Introducing Needle |  |
| Surface State Inside and Outside Parts |  |  | OK |  |
| Drawing Strength |  |  | OK |  |
| Heavy Metal Test (ppm) | <0.05 | <0.05 |  |  |
| Elongation Degree (cm) | 0.3 |  |  |  |
| Eluate Test |  |  |  |  |
| Appearance | * | * | * | Colorless, Transparent |
| pH | 0.2 | 0.3 | 0.2 | <2.0 |
| Heavy Metal Test | <0.01 | 0.01 | <0.01 |  |
| $KMnO_4$ Reducing Material (ml) | 0.3 | 0.2 | 0.3 | <2.0 mg |
| Distillation Residue (mg) | 0.1 | 0.1 | 0.2 | <1.0 mg |
| Test as Liquid Transfusion Test | Examples 11–13 | | | |
| Airtightness Test | OK | | | no air leakage |
| Acute Toxicity Test | normal | | | normal |
| Feverish Material Test | OK | | | OK |
| Hot and Cold Resistance Test | OK | | | OK |
| Adsorption of Nitroglycerin[1] | 0.499 ± 0.001 (wt %) | | | |
| Adsorption of Insulin[2] | 3.8 IU/ml ± 1 | | | |

Note:
*colorless and transparent

In the tests of Table 4, 1) and 2) were carried out as follows:

1) Adsorption of Nitroglycerin

When a nitroglycerin injection liquid (nitroglycerin/physiological salt solution=5 mg/10 ml, made by Eisai KK) was flowed at a flow rate of 1 to 1.5 ml/min through each of the parts of the liquid transfusion set of Examples 8 to 13, change of the nitroglycerin concentration was examined by a quantitatively determining method using a high speed liquid chromatography, as described in "Byoin Yakugaku (Hospital Pharmacy)" Vol. 12, 317 (1986) and "Iyaku Journal (Drug Journal)" Vol. 21, 113 (1985).

2) Adsorption of Insulin

When insulin (insulin 40, 40 IU/ml, made by Shimizu Seiyaku KK) was flowed at a flow rate of 1 to 1.5 ml/min through each of the parts of the liquid transfusion set of Examples 8 to 13, change of the insulin concentration was measured to examine the adsorption quantity of insulin by a quantitatively determining method using a high speed liquid chromatography, as described in "Byoin Yakugaku (Hospital Pharmacy)" Vol. 11, 432 (1985).

As shown in Table 4, any part of the liquid transfusion set of the present invention satisfies the standards. Measurement of the adsorption of a liquid medicament by an instrument, which has lately been considered to be a problem, is an item to examine whether a high grade medicament liquid is imparted to a human body in a precise quantity, and it will be clearly understood from the results of Table 4 that the molded articles of the cyclic resins of the present invention exhibit no or little adsorption of nitroglycerine and insulin.

It has been reported that PP, as a known material, exhibits adsorption of insulin in an amount of 7 to 8% by weight and nitroglycerin in an amount of 0.3 to 0.8% by weight, and PVC, as a known material, exhibits adsorption of insulin in an amount of 7 to 10% by weight and nitroglycerin in an amount of 13 to 15% by weight. As a countermeasure thereto, it has been proposed to add an adsorption inhibitor, for example, surfactants or amino acids, but the present invention does not need such an adsorption inhibitor.

Since the article of the present invention is a transparent resin article, the article is suitable for finding foreign matters or crystalline matters in a medicament liquid flowing through the dripping tube, coupling tube, etc. Bonding of the instruments or parts with each other can readily and strongly be effected.

As a test method of the chemical resistance of the synthetic resin, each of the instrument parts is immersed in a 0.5 weight % solution of sodium carbonate in an amount of 10 times as much as the weight of the each part, subjected to steam heating at a temperature of 121° C. for 30 minutes, and the solution is then subjected to measurement of the percent transmission of visible rays with a wavelength of 430 nm and 650 nm, thus obtaining a percent transmission of at least 90%. This means that the resin is excellent in chemical resistance.

Examples of the medical instruments according to the present invention will now be illustrated. The introducing needle 11 in FIG. 3 is formed of stainless steel. In FIGS. 4 to 6 are shown articles of the present invention and in FIG. 5, in particular, the introducing needle 11 and dripping cylinder 14 are coupled. FIG. 6 shows an example wherein an introducing needle with a larger size and larger length is used which is provided with a threaded part at the base so as to well couple with a discharge port of a plastic stopper and to prevent the introducing needle from coming out of a plastic bag or bottle even during dosing a liquid medicine for a long time.

In FIGS. 4–6, 11: introducing needle; 14: dripping cylinder; 22: stopper; 23: liquid port

EXAMPLE 14

Figure 7:
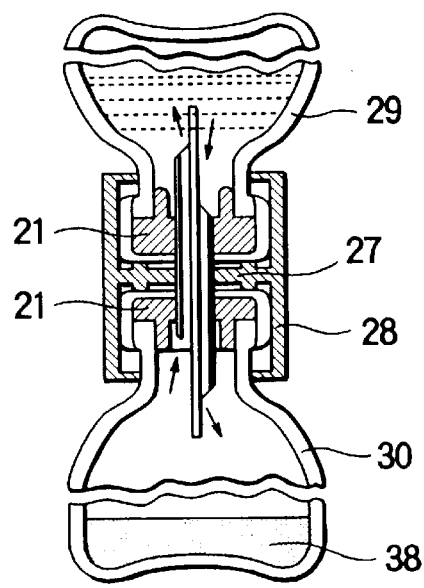
FIG. 7 is a cross-sectional view of a state such that a liquid is removed in a powdered medicament using a double headed needle mixer consisting of a cyclic resin according to one embodiment of the present invention.
Figure 8:
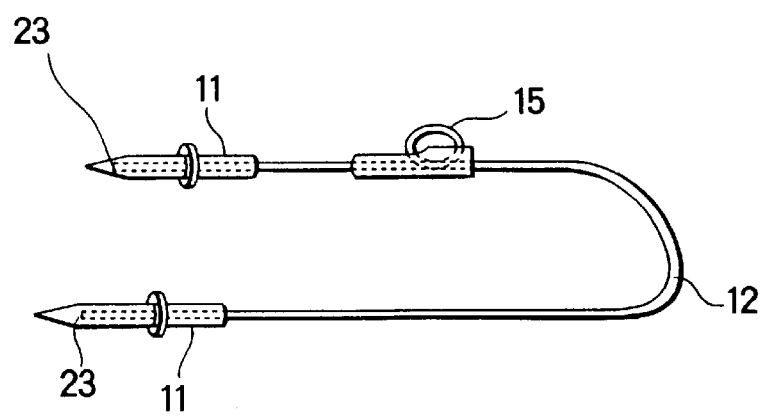
FIG. 8 is a cross-sectional view of a connector of transfer needles, consisting of a cyclic resin according to one embodiment of the present invention.

A transfuser (introducing needle, double-headed needle, transfer needle, Cf. FIG. 7 and FIG. 8) was formed of the resin of the present invention. This transfuser was used as an instrument for removing or transfusing for dissolving a transfusion liquid or dissolving liquid (e.g. pirified water) in containers of a glass bottle and glass vial, diamond vial and plastic bag, plastic bottle and glass vial, or plastic bag and plastic bottle, without exposing to the air, and for dosing a human body with a liquid medicament by the transfusion instrument of each of the foregoing Examples. For the preparation of a high calorie transfusion liquid, the transfuser was used for removing sanitarily a basic liquid (electrolyte such as purified water, physiological salt solution, etc.) for dissolving grape sugar, high concentration amino acids, various vitamines, etc. In FIG. 7 is shown a mode of using a transfuser, for example, a double headed needle having a liquid medicament path and air path for dissolving a powdered medicamnet in a glass bottle in distilled water for injection. In FIG. 8 is shown a coupling instrument for liquid transfusion comprising two introducing needles formed of the cyclic resin (b) of the present invention, combined with a coupling tube, and a discharge regulator at the middle part.

In FIG. 7, 21: rubber stopper; 24: partition plate; 25: air path in container; 26: liquid path; 27: base plate; 28: vial mouth holder; 29: vial for holding liquid; 30: vial for powdered medicament; 38: powdered medicament

EXAMPLE 15

Blood Bag

Figure 9:
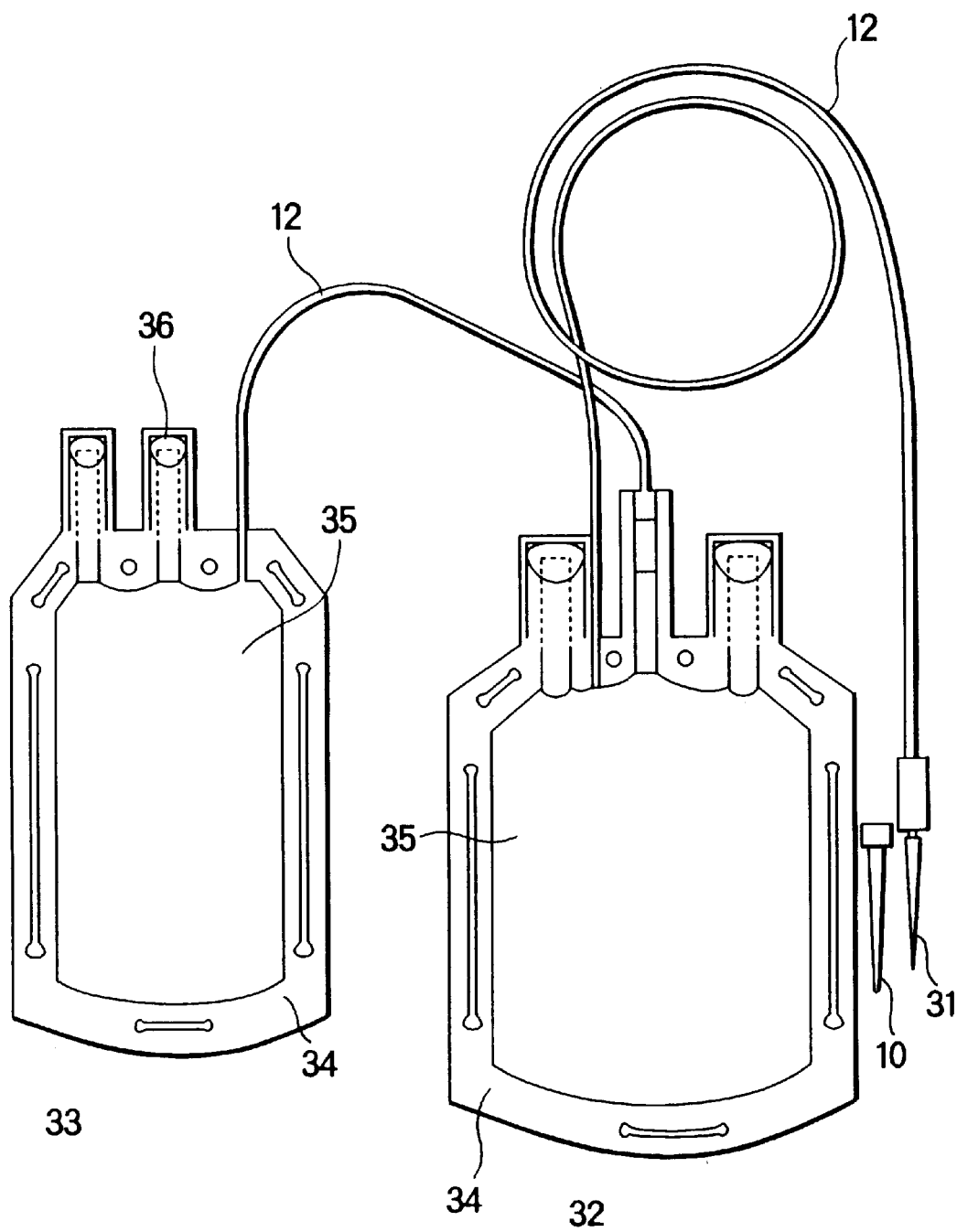
FIG. 9 is a cross-sectional view of blood bags consisting of a cyclic resin according to one embodiment of the present invention.

A container for storage of gathered blood, i.e. blood bag prepared according to the present invention is shown in FIG. 9, in which a blood gathering needle 31, coupling tube 12, parent blood bag 32 and at least one child blood bag 33 are combined. Blood is gathered from a human body by the blood gathering needle 31 and then stored in the parent blood bag 32 and child blood bag 33 after adding CPD (Citrate-Phosphate-Dextrose) liquid or ACD (Acid-Citrate-Dextrose) liquid for the storage thereof.

A blood holding part 35 was prepared by using a film having a thickness of 0.2±0.03 mm, consisting of a mixed resin of the cyclic resin (d) of the present invention or the cyclic resin (f) of the present invention with a saponified product of ethylene-vinyl acetate copolymer in a mixing ratio of 3:1 and heat sealing the peripheral seal part 34 of a blood bag by means of a high frequency thermocompression bonding machine. During heat sealing, a coupling tube 12 and exhaust port 36 were provided. As to the blood bag, there are test items based on vinyl chloride resin in the Official Notification Nos. 448 of the Ministry of Health and Welfare. When the bag was allowed to stand at a gauge pressure of 0.04±0.03 kg/cm$^2$ for 6 minutes according to the airtight test of these items, there was found no air leakage and when the bag was subjected to heat steam sterilization at a high pressure steam internal temperature of 121° C. and internal pressure of 1.1±0.1 kg/cm$^2$ for 20 minutes according to the pressure resistance test and heat resistance test of these items, there was found no abnormal phenomenon.

When the bag was further subjected to a test according to "49 Test Method of Plastic Container for Liquid Transfusion" of JP 12, it exhibited a value inside the test standard value and passed the standard.

EXAMPLE 16

Syringe-cum-Container Filled with Two Medicines in One Container

Figure 10:
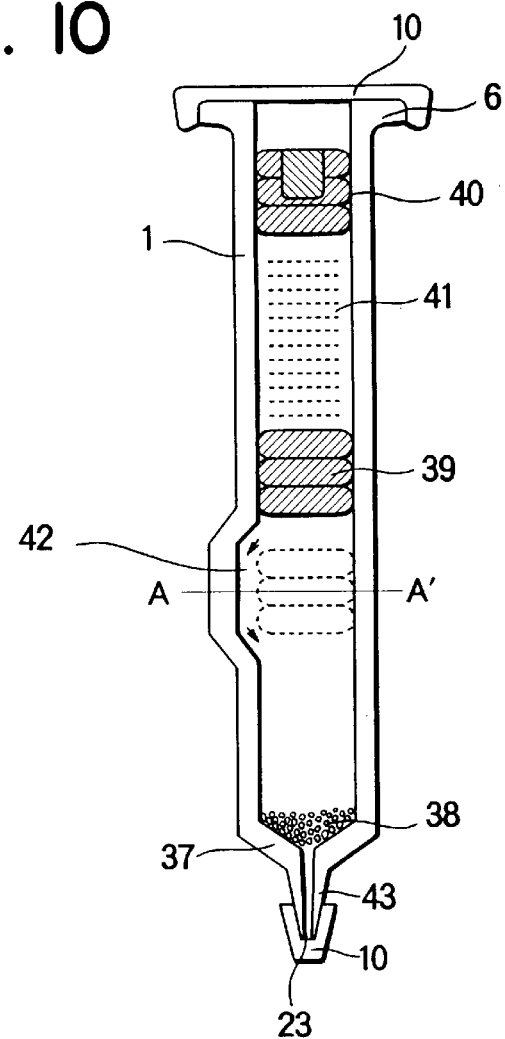
FIG. 10 is a cross-sectional view of a syringe-cum-container filled with two kinds of drugs, consisting of a cyclic resin according to one embodiment of the present invention.
Figure 11:
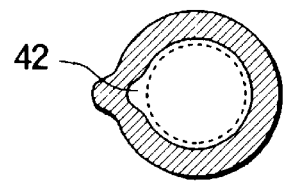

The mechanism of a syringe-cum-container (referred to as "container") filled with two kinds of medicines and formed of the cyclic resin of the present invention according to the present invention is shown in FIG. 10, in which a high concentration powdered medicament 38 is charged in a cylinder nozzle 37 of an injection barrel 1 and a bypass groove 42 is positioned at the end of the middle part of the injection barrel. As shown in A—A'cross-sectional view of the bypass groove 42 of FIG. 11, the thickness of the injection cylinder is rendered uniform and the outer circumference of the cylinder is rendered convex, i.e. the Inner wall Is enlarged at the middle part thereof to form the groove 42. A first sealing stopper 39 is substantially positioned at the middle part of the injection barrel 1 in the container, which is so designed that the thickness of the first sealing stopper 39 is less than the length of the bypass groove 42 and the stopper is completely embraced by the groove, as shown by broken line in FIG. 10.

A second sealing stopper 40 is positioned at the aperture of the injection barrel 1, the second sealing stopper 40 having a hollow into which the end of a plunger 2 is to be inserted, and distilled water or a dilute medicamnet liquid 41 is charged in between the second sealing stopper 40 and first sealing stopper 39. The aperture of the barrel 1 is provided with a flange 6 to be covered by a cap 10 to close the aperture. The nozzle end 37 of the injection barrel 1 is narrowly elongated to give a shape 43 of injection needle and the point is closed by a rubber cap 10.

When using a container medicament of this Example, the end of the push rod is connected with the second sealing stopper in the injection barrel and the plunger is forced in the injection barrel to push the distilled water and first sealing stopper. When the first sealing stopper is thus positioned in the bypass groove, the distilled water is flowed through the bypass groove, mixed with the powdered medicament 38 and dissolves the powdered medicament to form a liquid medicament with a concentration to be dosed. The thus diluted medicament liquid is dosed by the octopus tube 17 as shwon in FIG. 3 in many cases.

Production of the injection barrel was generally carried out by heating and melting at a temperature of 230 to 300° C. firstly an amorphous nylon (Novamid X 21—commercial name—made by Mitsubishi Kasei Kogyo KK) and secondly the cyclic resin (f) of the present invention, in a metallic mold of an injection barrel type, subjecting to injection molding and then cooling.

The first sealing stopper and second sealing stopper were prepared by blending 100 parts by weight of BR (BR 01—commercial name—made by Japan Synthetic Rubber Co., Ltd.) and 20 parts by weight of ultra-high molecular weight polyethylene powder (Hizex Million 240—commercial name—made by Mitsui Sekiyu Kagaku KK) as a raw material rubber, crosslinked by using an organoperoxide to adjust the hardness of the product to 48±5 and annular protrusions were formed on the surface of the rubber stopper.

When the syringe-cum-container was further subjected to a test according to "49 Test Method of Plastic Container for Liquid Transfusion" of JP 12, it exhibited a value inside the test standard value and passed the standard.

The medical instrument of the present invention is not intended to be limited to the foregoing specific examples.

The benefits or effects of the present invention are summarized below:

(1) Since the medical instrument of the present invention is formed of the specified cyclic resin, medicament liquids such as pharmaceuticals, nutriments can be maintained in high quality and dosed correctly and sanitarily.

(2) The cyclic resin is inert to acid or alkali solutions and meets with less stripping of fine particles, etc. from the surface of the medical istrument and less adsorption of medicament liquids on the surface thereof, thus having a high sanitary property.

(3) Influences upon medicaments by individual or overall external factors i.e. environments such as heat, oxygen, air, humidity (moisture), lights (ultraviolet rays) and the like, and outer forces can be reduced.

(4) The medical instrument of the present invention stands the test standards for medical instruments provided by JP 12 and Official Notification of the Ministry of Health and Welfare, etc.

(5) Molding of the medical instrument of the present invention can readily be accomplished.

That is, the present invention provides a sanitary medical instrument having the foregoing features and serves to the industry to a great extent.

What is claimed is:

1. A medical device comprising a molded article having an outer wall defining an inner space to hold a fluid, said molded article comprising a resin comprising a cyclic olefin compound or a bridged polycyclic hydrocarbon compound, wherein the cyclic olefin compound is at least one member selected from the group consisting of monocyclic olefin compounds, alkyl derivatives of monocylic olefin compounds, and acrylate derivatives of monocyclic olefin compounds, wherein the bridged polycyclic hydrocarbon compound has at least one unsaturated bond in the ring or in a substituent thereof, wherein the content of the cyclic olefin compound in the molded article is at least 30 weight percent, and wherein said resin is molded and not laminated.

2. The medical device according to claim 1, wherein the resin further comprises at least one copolymer member selected from the group consisting of lower olefins, aromatic compounds, vinyl monomers of lower olefins, and vinyl monomers of aromatic compounds.

3. The medical device according to claim 1, wherein the resin is a mixture comprising the cyclic olefin compound or the bridged polycyclic hydrocarbon compound and at least one copolymer member selected from the group consisting of non-cyclic olefinic resins and synthetic rubbers.

4. The medical device according to claim 1, wherein the resin has a bromine number of at most 1.

5. The medical device according to claim 1, wherein the resin has a softening point of at least 90° C.

6. The medical device according to claim 1, wherein the article comprises at least one laminated layer made from the resin.

7. The medical device according to claim 1, wherein the article is an injection barrel.

8. The medical device according to claim 1, wherein the article is a transfuser.

9. The medical device according to claim 1, wherein the article is a liquid transfuser set component.

10. The medical device according to claim 1, wherein the article is a blood gathering instrument.

11. The medical device according to claim 1, wherein the article is a blood transfusing instrument.

12. The medical device according to claim 1, wherein the article is a blood set part.

13. The medical device according to claim 1, wherein the article is a kidney dialysis device.

14. The medical device according to claim 1, wherein the article is a catheter.

15. The medical device according to claim 1, wherein the article is a tube.

16. The medical device according to claim 1, wherein the article is a combined syringe and container.

17. The medical device according to claim 1, wherein the article contains a needle.

18. The medical device according to claim 1, wherein the molded article is produced by injection molding.

* * * * *